United States Patent [19]
Smith et al.

[11] Patent Number: 5,147,294
[45] Date of Patent: Sep. 15, 1992

[54] THERAPEUTIC METHOD FOR REDUCING CHRONIC PAIN IN A LIVING SUBJECT

[75] Inventors: Ivor S. Smith, Brookline; Timothy J. Stafford, Boston, both of Mass.

[73] Assignee: Trustees of Boston University, Boston, Mass.

[21] Appl. No.: 590,904

[22] Filed: Oct. 1, 1990

[51] Int. Cl.$^5$ ............................................. A61M 31/00
[52] U.S. Cl. ................................... 604/49; 128/898; 604/20
[58] Field of Search .................. 604/19, 20, 48, 49; 128/898

[56] References Cited
U.S. PATENT DOCUMENTS

| | | | |
|---|---|---|---|
| 4,622,219 | 11/1986 | Haynes | 424/38 |
| 4,725,442 | 2/1988 | Haynes | 424/490 |

*Primary Examiner*—Stephen C. Pellegrino
*Assistant Examiner*—Michael Rafa
*Attorney, Agent, or Firm*—David Prashker

[57] ABSTRACT

The present invention provides a therapeutic methodology for the treatment of chronic pain from its earliest stages to the most severe and intractable stage in a living subject. The therapeutic methodology is able to provide substantial pain relief over long time duration to patients afflicted with chronic pain; and relief from chronic pain and improvement of all symptoms coincidental with chronic pain begins immediately upon treatment. The therapeutic procedure must be performed by a properly trained medical practitioner or clinician within the confines of a hospital setting. Nevertheless, the therapeutic method provides pain relief for chronic pain sufferers, especially those persons who have been unable to obtain relief from chronic pain despite drastic medication and other pain relief techniques.

11 Claims, No Drawings

THERAPEUTIC METHOD FOR REDUCING CHRONIC PAIN IN A LIVING SUBJECT

FIELD OF THE INVENTION

The present invention is concerned generally with the alleviation of pain; and is particularly directed to therapeutic methods for reducing and curing chronic pain in a living subject.

BACKGROUND OF THE INVENTION

Pain is the most common symptom for which patients seek medical assistance and relief, and chronic pain is among the most vexing problems that physicians face. In general, pain has two aspects: the first is a non-emotional perception of a stimulus or event which is usually strong enough to produce tissue damage to the person; the second is the individual's personal response to the perception of that stimulus or event. Pain implies damage to the human organism, whether physical or psychological; and chronic pain, if untreated, will itself cause damage to the living body.

For these reasons, the clinician normally questions his patient regarding the characteristics of the pain. A carefully elicited history of pain will include the chronology, nature, location, radiation of pain, and any other factors that aggravate or alleviate pain. Pain is a highly subjective phenomenon and the patient's description may often be difficult to interpret objectively. Individual reactions to pain are extremely variable, often being influenced by many psychosocial and cultural factors. It is therefore essential for the clinician to establish not only the primary cause (e.g., trauma or infection) and pathogenesis (e.g., inflammation or anoxia) of the pain, but also any significant contributing factors (e.g., anxiety or secondary gain).

Symptomatically, pain may be local or diffuse; constant or intermittent; sharp or dull; and acute or chronic. The sensing organs for pain are the naked nerve endings found in almost every tissue of the body. Pain impulses are transmitted to the central nervous system by two fiber systems. One system is made up of small, myelinated somatic nerve fibers which conduct pain quickly; the other comprises unmyelinated nerve fibers which conduct pain impulses more slowly. The presence of these two pain pathways, one slow and one fast, has been proposed as the explanation for the physiological observation that there are two kinds of pain. A painful stimulus causes a "bright, sharp, localized" sensation which is typically followed by a "dull, intense, diffuse" unpleasant feeling. These two sensations are variously called fast and slow pain or first and second pain.

Pain is also clinically identified as being either acute or chronic. A common view holds that the difference between acute and chronic pain can be described by the duration of the pain. Pain lasting over six months in duration is typically considered chronic; and any shorter time period of pain is usually considered acute. Several other clinical features are also traditionally used to differentiate acute pain from chronic pain. Patients suffering from severe acute pain often give a clear description of its location, character, and timing. Also, acute pain usually responds well to analgesic agents; and the psychological makeup of the patient often plays only a minor role in the pathogenesis. In contrast, patients suffering from chronic pain typically are unable to describe precisely the location, character, and timing of the pain. Furthermore, chronic pain often is less responsive to analgesic agents; and the individual's psychologic state has a larger role. The clinician's dilemma thus is increased since there are no reliable, objective tests by which to assess chronic pain. For the reasons, the physician normally accepts his patient's report, taking into consideration his age, cultural background, environment, and other psychologic background factors known to alter a person's subjective reaction to pain.

Physicians also conventionally divide chronic pain into three somewhat overlapping categories in decreasing order of frequency. These are: psychophysiological disorders; chronic pain associated with structural disease; and somatic delusions. Psychophysiological disorders are those in which psychological factors have engendered chronic physiological alterations which produce pain long after the underlying cause has healed. Structural disease, such as a herniated disc or torn ligament, may once have been present; but whether structural disease was ever present or not, the pain continues chronically long after the organic disorder has disappeared. Such persons tend to respond poorly to analgesic drugs, but often respond well to combination therapy directed against the organ tissue and at the disturbing psychological factors.

Chronic pain associated with structural disease may be characterized by prolonged episodes of pain such as occurs with rheumatoid arthritis, metastatic cancer, or sickle cell anemia. The patient may have prolonged episodes of pain alternating with pain-free intervals; or display unremitting pain which varies in severity. Psychological factors may play an important role in increasing or relieving pain, but the treatment of the chronic pain by analgesics or correcting the underlying disease is typically more helpful.

The category of somatic delusions represents pain caused by neither structural nor physiological disorders. Such pain occurs in patients with profound psychiatric disturbances such as psychotic depression or schizophrenia. The history of the pain is so vague and bizarre and the distribution of the pain is typically so unanatomical as to suggest this category. Such persons respond only to psychiatric therapy; and the management of pain must be pursued with this causation in mind. It will be recognized that these divisions represent the conventional theoretical classifications of chronic pain for purposes of clinical diagnosis of painful disorders.

The physician confronted with a person complaining of chronic pain thus normally follows the accepted principles for providing pain relief. These commonly include correcting the cause of pain; individualizing therapeutic treatment; and selecting appropriate analgesics. Clearly, measures directed at eliminating the true cause of pain deserve the first consideration. Pain relief can only be achieved by modifying or suppressing the primary disease process; and the hazards of administering analgesics without first attempting to establish a diagnosis can not be overemphasized. Analgesics, particularly narcotics, may mask the symptoms of serious illness.

The symptomatic management of pain is dependent upon its severity and cause. The relief of chronic pain is often perplexing and difficult because measures useful in the treatment of acute pain are often ineffective for chronic pain. It is often necessary to resort to a combination of indirect and multidisciplinary therapeutic methods in order to provide any sort of relief whatsoever. These include the following:

Analgesics: The use of analgesics includes nonaddictive formulations, narcotics, and sometimes antidepressant drugs in low doses. The nonaddictive analgesics employed include salicylates such as aspirin; acetominophen; and newer nonsteroidal, anti-inflammatory drugs such as indoleacetic acids, oxicams, and proprionic acids. The potentially addictive analgesics include codeine, propoxyphene, agonist-antagonist opioids; and morphine. The antidepressant drugs include monoamine oxidase inhibitors; tricyclic antidepressants; or the newer cyclic drugs which include maprotiline, trazodone, and nomifensine [Clinical Pharmacokinetics of Analgesic Drugs, (Prithri, R. P., editor), Yearbook Medicall Publishers, 1986, pp 503-538].

A second approach to alleviating chronic pain utilizes the numerous psychological techniques such as hypnosis, operant conditioning, biofeedback, progressive relaxation, distraction, and placebo therapy. Each of these have had varying degrees of success in relieving chronic pain [Textbook of Pain, (Wall and Melzack, editors), 2nd edition, 1989, pp 989-1031].

A third approach has been the use of transcutaneous electrical nerve stimulation or "TENS" of which many varieties of apparatus are commercially available today. This technique employs the use of electric current to stimulate the peripheral or central nerves of the body and is said to be a simple and effective means of relieving well-localized chronic pain for some patients Unfortunately, the success and relief of pain varies markedly from person to person [Deyo et al., New Eng. J. Med 322:1627-1634 (1990)].

A recently adopted procedure for chronic pain treatment employs acupuncture. While the mechanism of relief remains uncertain (and sometimes criticized by different medical authorities), the use of acupuncture sometimes does provide relief for the chronic sufferer [Textbook of Pain, (Wall and Melzack, editors), 2nd edition, 1989, pp 906-919].

A variety of different neurosurgical procedures including chordotomy and deep brain electrical stimulation are sometimes considered where the patient has severe, chronic pain. The value of these procedures for the treatment of chronic pain is unfortunately often in doubt [Textbook of Pain, (Wall and Melzack, editors), 2nd edition, 1989, pp 768-883].

A more common procedure often employed is the use of sympathetic nerve blockade in which local anesthetic agents reversibly block nerve impulse conduction when introduced into the central nervous systems. Via different techniques, the local anesthetic agent is applied to sympathetic nerves in the subarachnoid space, the epidural space, or ganglia by syringe. These procedures and techniques have been employed for approximately seventy years as treatments for intractable visceral pain states such as chronic pancreatic pain or chronic pain from a visceral malignancy [Management of Pain, (Bonica, J. J., editor), Lea and Febiger, 1953, pp 371-456].

In addition to all the forgoing approaches and techniques described, the scientific literature is replete with reports of experiments and unusual techniques for the treatment of chronic pain syndromes. The difficulty with such reported techniques and modes of chronic pain treatment is that the reported experiment or history of chronic pain treatment is not viewed by other practitioners, physicians, or medical research as a viable alternative; and the isolated report and technique remains limited both in usage and availability to only a few persons outside the original research group which first identified it for use.

To factually demonstrate this anomaly, the treatment of chronic pain via iontophoresis of vinca alkaloids onto the skin of patients stands as but one outstanding example. Of the four chemically similar vinca alkaloids, only two—vinblastine and vincristine, have recently received some clinical investigation. The vinca alkaloids are extracts of the periwinkle plant and were first recognized to show activity against an acute lymphocytic neoplasm in mice. The therapeutic uses clinically produce beneficial responses in various lymphomas and leukemias and act as agents against carcinomas of the breast, lung, oral cavity, testis, and bladder. In the early 1980's, a Hungarian research group reported the treatment of chronic pain syndrome using iontophoresis of vinca alkaloids [Csillik et al., Neuroscience Letters 31:87-90 (1982)]. Subsequently, a report of iontophoresis administration of vinca alkaloids in the treatment of postherpetic pain was published by an Italian research group [Rossano et al., The Pain Clinic 3:31-36 (1989)]. Each publication reported the effective treatment of pain for its patients without causing major physiological changes. Neither publication and report was able to go beyond the immediate clinical treatments described; and insofar as is presently known, there has been no follow up whatsoever either to confirm or improve the basic reports described within each of these publications.

The major difficulties, therefore, with all the previously described conventionally known techniques said to be effective in the treatment of chronic pain are thus two-fold in nature. First, the primary purpose for most of the conventionally known procedures and therapeutic regimens is intended for the treatment of acute pain primarily—the techniques of which have then been fostered onto the treatment of patients with chronic pain as an additional possible application. Accordingly, none of the conventionally known treatments were intended for use in the treatment of chronic pain specifically; and none are directed to alleviating the poorly localized, ill defined character, and inconsistent timing of chronic pain. Second, as generally recognized and appreciated by clinicians and medical researchers alike, the conventionally known therapeutic treatments and regimens for treating chronic pain are highly subjective and individual in their efficacy; irregular and inconsistent in providing any relief whatsoever; and are as likely to fail as to succeed in providing any pain relief at all.

It is precisely for this failure to expect good results that many medical authorities strongly advise and recommend the use of a combination of indirect and multi-disciplinary therapeutic methods—none of which is expected to work alone and very few of which are consistently effective even in combination. The clinician must proceed in a trial and error mode approach in treating the chronic pain sufferer, eliminating those which appear to provide little or no relief while concentrating and emphasizing those which sporadically appear to provide some therapeutic effect. Worst of all, it is generally agreed among practitioners and clinicians that despite all of the presently known methods and techniques, a very substantial number of persons suffering from chronic pain will find no meaningful relief whatsoever; and be compelled merely to endure the chronic pain as best they can. For all these reasons, it will be recognized and appreciated that a therapeutic method will provide effective and immediate long-term relief to person afflicted with chronic pain would be seen as an outstanding advance and major improvement in therapeutic methods.

SUMMARY OF THE INVENTION

A therapeutic method for alleviating sympathetically mediated chronic pain in a living subject, said therapeutic method comprising the steps of:

identifying the anatomical area of the living subject from which the chronic pain originates as being mediated by the sympathetic nervous system;

initiating at least one sympathetic nerve block in the living subject such that the part of the sympathetic nervous system innervating said chronically painful anatomical area becomes blocked and unable to conduct a nervous impulse for a predeterminable time; and administering at least one antagonist of nerve growth factor to the living subject whereby said administered antagonist substantially nullifies the neuron stimulation effect of such nerve growth factor as is present at said chronically painful anatomical area.

DETAILED DESCRIPTION OF THE PREFERRED METHODOLOGY

The present invention is an improved therapeutic methodology for the alleviation—that is, the substantial reduction or elimination—of sympathetically mediated chronic pain. The efficacy of this invention is dependent upon the presence of two conditions: a diagnosis by the medical practitioner or clinician that his patient suffers from chronic pain; and the diagnostic determination by the medical practitioner or clinician that the chronic pain is mediated by—that is, controlled, influenced, or affected by—the sympathetic neurons of the autonomic nervous system. Given these underlying qualifications and conditions, patients having a history of intractable, chronic pain will be able to achieve substantial relief for a variable, but extensive time duration.

In order to properly and completely understand the steps of the present therapeutic methodology, the reader must be at least familiar with, and preferably conversant and comfortable with, the neuroanatomy and functional neurology of the human body; the physiology of neurons and transmission of nerve impulses to and from the central nervous system and the peripheral nervous system; the pathology and diagnosis of sensory dysfunction and pain disorders; and the current pharmacological therapies and medical modes of treatment for pain. A summary review has been provided within the background subject matter previously disclosed herein. A more detailed review and minute description is provided by the following texts, each of which is individually expressly incorporated by reference herein: Joseph G. Chusid, *Correlative Neuroanatomy & Functional Neurology*, Lange Medical Publications, Los Altos, California, 1985; William F. Ganong, *Review Of Medical Physiology*, Lange Medical Publications, Los Altos, California, 1985; Crupp Chatton and Tierney, *Current Medical Diagnosis & Treatment* 1986, Lange Medical Publications, Los Altos, California, 94022; *Essentials Of Medicine*, W. B. Saunders Company, 1986; P. PrithviRaj, *Practical Management Of Pain*, 1986; *Pain, Discomfort, and Humanitarian Care* (Bonica, J. J., editor), Elsevier Publishing, New York, 1980; *A Synopsis Of Anesthesia*, 10th edition, 1987; *Textbook Of Pain*, Wall and Melzack, editors), 2nd edition, 1989; and *The Management of Pain*, (Bonica, J. J., editor), Lea and Febiger, 1953.

Furthermore, in order to avoid any ambiguity, vagueness, or misnomers regarding the proper terminology, jargon, or nomenclature regarding neuroanatomy, diagnostic or clinical approaches, or medical therapies and regimens, a non-comprehensive listing of terms, definitions, and descriptive information is provided. Unless otherwise stated, these terms and definitions will be employed uniformly herein.

Neuron (or nerve cell): any of the excitable cells of the nervous system that are concerned with the reception, integration, and transmission of information. A neuron typically consists of a nerve cell body with branding dendrites or receptor membranes that conduct impulses toward the cell body; and an axon or fiber, the greatly elongated process which conducts impulses away from the cell body.

Afferent neuron: any neuron that conducts a nervous impulse from a peripheral sensory receptor toward the central nervous system.

Efferent neuron: any neuron that conducts a nervous impulse from the central nervous system to an organ of response.

Somatic sensory neuron or fiber: any afferent somatic neuron possessing a sensory function such as pain which delivers impulses arising from various receptors in the body to the central nervous system.

Somatic motor neuron or fiber: any efferent somatic neuron that conducts impulses from the central nervous system to voluntary skeletal muscles.

Autonomic preganglionic neurons or fibers: efferent neurons whose cell bodies lie in the central nervous system and whose axons terminate in the autonomic ganglia.

Autonomic postganglionic neurons or fibers: efferent neurons whose cell bodies are situated in the autonomic ganglia and whose axons extend to relay impulses beyond the ganglia.

Central nervous system: that portion of the nervous system consisting of the brain and spinal cord.

Peripheral nervous system: the division of the nervous system composed of the nerves and ganglia outside the brain and spinal cord. It is itself divided into the somatic and autonomic systems.

Somatic nervous system: the part of the peripheral nervous system composed of somatic sensory and motor neurons; and which transmits impulses from the afferent sensory neurons outside the brain and spinal cord to the central nervous system and transmits other impulses via efferent motor neurons to the voluntary muscles of the body. Most somatic neurons are myelinated fibers which vary in overall diameter from 2-20 $\mu$; these myelinated fibers are often termed "A fibers" and are themselves subdivided into four groups according to decreasing size and termed alpha, beta, gamma, and delta respectively. Largest are alpha fibers, related to motor function, proprioception, and reflex activity. Beta fibers also innervate muscle and transmit touch and pressure sensations while gamma fibers control muscle spindle tone. The thinnest A fibers, the delta group, subserve pain and temperature functions and signal tissue damage. These delta A fibers are only 2-5 $\mu$in diameter and conduct impulses rapidly at rates of 12-30 meters per second. Some somatic neurons are also "C" fibers as described below.

Autonomic nervous system (or "ANS"): the part of the peripheral nervous system that regulates the activity of the viscera via autonomic efferent neurons and is itself composed of two divisions, the sympathetic system and the parasympathetic system. By definition, the ANS is entirely an efferent system and it is "automatic" in the sense that most of its functions are independent of conscious thought. Within the entire autonomic nervous system as a whole, a two-neuron chain characterizes the organization of the autonomic nerves, a chain composed of pre- and post-ganglionic neurons. The preganglionic neurons have their cell bodies in the brain or spinal cord; and their axons terminate on nerve bodies or ganglia within either the thoracic or the abdominal cavity, or in close proximity to or in a visceral organ. The preganglionic neurons are thinly myelinated nerve fibers having a diameter of 1–3 $\mu$ and are known as "B fibers". The axons of the B fibers innervate vascular and intestinal smooth muscle, among others; the B fibers are thus extremely important during spinal anesthesia. In complimentary fashion, the postganglionic neurons originate in the ganglia and terminate directly on the circulatory system, cardiac muscle, smooth muscle, or glandular tissue. The postganglionic neurons are unmyelinated nerve fibers having a diameter of less than 1 $\mu$ and are termed "C fibers". The non-myelinated C fibers (like the myelinated delta group A fibers of the somatic system) subserve pain and temperature transmission but have a much slower impulse conduction velocity of only 0.5–2.0 meters per second.

Most visceral organs are innervated by both the sympathetic and parasympathetic systems of the ANS. However, the adrenal medulla, spleen, pilomotor muscles, sweat gland, and blood vessels of the viscera, skin, and skeletal muscle are innervated only by the sympathetic division. Generally, where dual innervation exists, the sympathetic and parasympathetic systems act antagonistically; the activity of the parasympathetic system promotes vegetative function while the activity of the sympathetic system favors those functions necessary for vigorous muscle activity.

Sympathetic nervous system: in this division of the ANS, the efferent preganglionic fibers arise from cells within the first thoracic to second and third lumbar segments of the spinal cord. The synaptic neurotransmitter of preganglionic B fibers within ganglia is acetylcholine. The postganglionic C fibers terminate in the cardiac and smooth muscle or glandular tissue; the neurotransmitter of the post-ganglionic C fibers is various between acetylcholine or norepinephrine depending upon location. An exception is the adrenal medulla which does not have a postganglionic C fiber; instead, its B fibers release norepinephrine and epinephrine directly into the systemic circulation.

Parasympathetic nervous system: the efferent preganglionic B fibers of the parasympathetic system emerge from the brain in cranial nerves III, VII, IX, and X (oculomotor, facial, glossopharyngeal, and vagus nerves, respectively) to supply visceral structures in the head, thorax, and abdomen; and from the second, third, and fourth sacral spinal nerves to supply the pelvic viscera. The preganglionic B fibers in both the crania and sacral outflows synapse within ganglia on short postganglionic neurons that are in close proximity to, or are distributed within, the visceral structures they supply. The synaptic neurotransmitter for both the pre- and post-ganglionic fibers is the same, acetylcholine.

I. Definition And Description Of Chronic Pain

The present invention is a novel development and major departure from most conventionally known theories regarding pain, especially chronic pain in the living subject. The underlying basis and rationale for the present therapeutic methodology depends on several different unique premises and interactions. First and foremost, chronic pain is deemed to be a secondary development and occurrence which chronologically follows a true organic injury, disease, or disorder. In this respect, the present invention disregards the existence of that conventional category known as "somatic delusions" which is said to be a chronic pain condition which is caused by neither structural nor physiological disturbances in the patient, but is said to be the result of psychiatric disturbances such as psychotic depression or schizophrenia. On the contrary, the present methodology demands the existence of an original organic structural disease, organic disorder, or tangible physical abnormality as the underlying causative event in a patient's medical history in order that even the possibility of a chronic pain condition occur. The original injury may take the form of a physical trauma; autoimmune disease; an infection; a neoplastic disease; a metabolic disease or disorder; or any other kind of organic injury or abnormality recognized as a pathological condition within a living subject. The original physical injury may affect any region or tissue of the body. Moreover, the original organic injury or abnormality may be long-term or short-term in duration; and may exist on a continuing or concurrent basis with the subsequent development of chronic pain as such. Accordingly, it is only necessary that a prior organic injury, infection, disorder, disease, or other abnormality have existed as a discrete and identifiable event; it is inconsequential to the present invention whether or not the original organic change continues to exist or has been eliminated (i.e., cured, healed, removed, or repaired) at the time when chronic pain appears to afflict the patient.

Second, chronic pain can be identified as originating from a specific or localized anatomical area. Although the patient typically can not precisely describe the localization, character, and timing of chronic pain—its existence chronically is both real and substantial to the individual. The now classic Hippocratic definition of pain as "the absence of pleasure" remains today the best definition for chronic pain. Since chronic pain is a subjective phenomenon and difficult to objectively measure, the physician must believe his patient regarding the quality, duration, and severity of the chronic pain.

Third, the therapeutic methodology comprising the present nvention is based and relies upon the premise that most chronic pain is at least partially sympathetically mediated—that is, the sympathetic nervous system influences and partially controls the generation of chronic pain at the anatomical area or site from which the chronic pain appears to originate. The influence and control of the sympathetic nervous system is only partial however; the involvement of afferent sensory nerves and chemical mediators such as nerve growth factor as are present at the anatomical area provides the other causative half of the repetitious cycle of events which accounts for the perception of chronic pain in the patient. Moreover, the sympathetically mediated chronic pain may be accompanied by a number of other symptoms and complications. These include: dysesthesia (pins and needles, numbness, and allodynia); swelling or edema at the anatomical site; dysfunction of the tissues or organs; dystonia, a weakness or spasticity; discoloration of the anatomical area (red, blue, black, or pale coloring); a measurable temperature change in the patient (an increase or decrease, whether subjective or objective); mirror-image pain; distant changes (dry hair and brittle nails); and changes in sweating patterns or glandular tissue in general. These changes may appear individually or as a combination of these symptoms and clinical signs. It will be noted also that typically "psychological changes" such as anxiety and/or depression follow the pattern of chronic pain development.

Fourth, sympathetically mediated chronic pain often will follow a course of development into several stages, each of which is increasing more severe and debilitating. The stages can be diagnosed and objectively ascertained by using the conventionally known procedure of a sympathetic nerve block—that is, either the spinal cord or the paravertebral ganglia. As described in greater detail hereinafter, sympathetic nerve blocks or blockade employ local anesthetic agents which reversibly block nerve impulse conduction when applied to the spinal cord or the surrounding ganglia. The use of sympathetic nerve blocks also therefore serves as an objective tool for the early diagnosis and staging of chronic pain. Accordingly, first stage chronic pain is identified by the alleviation, or even curing in some instances, of chronic pain via the application of a *single* sympathetic nerve block to those specific nerves innervating that anatomical area from which the chronic pain originates. In the second stage chronic pain situation, repeated sympathetic nerve blocks are required over intervals of time in order to provide pain relief or, in some instances, a cure. The third stage of chronic pain is intractable—that is, a pattern of progressively increasing intervals of relief does not occur. This third stage of intractable pain is also marked by vasoconstriction of the blood vessels in the area of pain; and by a pattern of hyperactivity and decreased blood perfusion in sensory and sympathetic nerves and ganglia.

Fifth, sympathetically mediated chronic pain is the result of sympathetic neuron hyperactivity at the localized site of pain, regardless of tissues or organs involved. As will be described hereinafter, the neural hyperactivity extends to not only sympathetic nerves, but also involves afferent sensory nerves—both of which have been stimulated into a hyperactive state by the presence of a chemical mediator such as nerve growth factor at the anatomical area or site from which the chronic pain originates. Abnormal hyperactivity of the sympathetic nervous system at the local anatomical site is commonly a part of the cause of chronic pain regardless of which stage of development presently exists for the patient.

II. Cyclic Mechanism Believed Responsible For Sympathetically Mediated Chronic Pain The underlying biological mechanism believed responsible for the occurrence and development of chronic pain in a living subject is a repetitious cycle of events and biological reactions following true organic trauma, disease, or disorder. The original injury—be it a physical trauma, a disorder, a disease, or any other recognized abnormal or pathological state—initiates a sequence of events which allows, but does not require or demand, the subsequent development of chronic pain in the patient. A local site or locus of injury at a particular anatomical area causes a derangement of or abnormality within local tissues and/or organs. In many instances, the original organic injury or abnormality results in a conduction of impulses by the afferent sensory neurons of the peripheral nervous system which is registered as pain in the brain of the patient. The physical change or derangement of the tissues and/or organs, particularly if severe or of long duration, causes at least one fundamental modification in the local anatomical area in addition to the typical abnormalities and changes characteristic of the original organic injury itself. The critical event is the synthesis and release into the immediate anatomical area by the damaged or abnormal cells and tissues of a specific polypeptide which has been identified and characterized as nerve growth factor or "NGF".

Nerve growth factor has been extensively studied by research investigators because of its unique property in causing a trophic effect on both sympathetic nerves and fibers as well as upon sensory nerves and fibers; and because it is able to initiate a hyperactive state on neurons generally within a localized area which causes them to grow. The important properties and characteristics of nerve growth factor may be summarized as follows: nerve growth factor is a polypeptide comprised of 118 amino acids in the monomer form and has a molecular weight of about 30,000 daltons in the dimer state. Several different formulations of nerve growth factor are known. The active molecule is a dimer comprised of two alpha and two gamma units. Nerve growth factor is secreted by all cells, some in greater quantities than others; and it is produced at all possible sites of tissue injury in the living subject. Although the true cells responsible for synthesis and release of NGR is still a matter of controversy, nerve growth factor is taken up by specific receptors in the axons of sympathetic fibers and sensory fibers and is transported up the fiber in retrograde fashion to the neural cell body. An excess of this polypeptide then stimulates the neuron cell body into a hyperactive state. More detailed information regarding nerve growth factor, its characteristics, and its ability to initiate a hyperactive, stimulatory state in sensory and sympathetic neurons may be found in the following publications, the texts of which are each explicitly incorporated by reference herein: Levy-Montalcini, R. and P. Calissano, *Scientific American* 240:68–77 (1979); Levy-Montalcini et al., *Progress In Neuroendocrine Immunology* 3:1–10 (1990); Windebank, A. and J. Poduslo, *Brain Research* 385:197–200 (1986); Sidney Ochs, *Axoplasmic Transport And Its Relation To Other Nerve Function,* John Wiley and Sons, New York, 1982; Kessler, J. and I. Black, Proc. Natl. Acad. Sci. U.S.A. 77:649–652 (1980); Khan et al., *Journal of Neuroscience Research* 18:562–567 (1987); Goedert *et al., Proc. Natl. Acad. Sci. U.S.A.* 78:5895–5989 (1981); Korshing, S. and H. Thoenen, *Neuroscience Letters* 39:1–4 (1983); and the references cited within each of these specific publications.

While it may be that some level of NGF production peripherally coupled with retrograde axonal transport is necessary for the maintenance of function for neurons, cellular injury within a tissue or organ results in an increased production and transport of NGF. An excess production of nerve growth factor then stimulates the neuron cell body into a hyperactive state; and the continued excess production of nerve growth factor will cause a repeated and increasing stimulation effect and hyperactivity of both sympathetic neurons and somatic sensory neurons. Stimulation of the cell bodies of sensory afferent neurons in the dorsal root ganglia results in changes in a subpopulation of these neurons including the increased production of Substance P. Stimulation of efferent sympathetic neurons results in trophic effects, increasing size, and the production of tyrosine hydroxylase—a key enzyme in the production of norepinephrine, the effector chemical released at the endings of these sympathetic efferent neurons. The overly prolonged neuron stimulation effect and the ever-increasing state of hyperactivity for sympathetic and somatic sensory nerves at the localized anatomical site will continue indefinitely until the nerve growth factor itself is removed or nullified by an antagonist.

In the initiation of chronic pain in the living subject, it is the uptake of never growth factor, present in excess at the local site of injury, by the receptors on the axons of the sympathetic neurons and the sensory neurons which begins the vicious, repetitious cycle of events causing the development and stage progression of chronic pain. While acute pain is conventionally believed to involve the somatic afferent sensory pathways alone, the present invention holds that chronic pain involves not only the somatic afferent sensory pathways but also the sympathetic efferent system and includes visceral afferent pathways. Moreover, the present invention holds that the persistence of chronic pain described symptomatically as a "viscous cycle" involves a coupling of both these afferent and efferent pathways when stimulated into hyperactive states. Physical signs observed at the site of injury at different stages of pain duration (such as vasoconstriction, spread, etc.) correspond to a number of distinct anatomical or chemical events involving either or both of these nerve pathways.

Blockade of the sympathetic nerve tract alone using local anesthetics is by necessity short-term if effective and is efficacious only in early distrophies. Investigative research by other has shown that NGF blockade percutaneously can also be efficacious, but the method requires long-term, repeated applications. The present invention maintains that sympathetic blockade coupled with NGF antagonism by any effective means act together to produce far more efficacious and longer lasting relief from chronic pain.

The present therapeutic methodology is thus the direct outgrowth and implementation of steps to disrupt and eliminate both halves of the repetitive, cyclic nature of chronic pain. Since the cycle has two major parts which follow one another seratim, it is deemed insufficient and ineffective to eliminate or disrupt only the stimulatory effect of the nerve growth factor t the localized anatomical area alone; or to cause an inability of the central nervous system to send efferent signals and electrical impulses via the sympathetic nervous system back to the local anatomical area. Accordingly, to be truly therapeutic and efficacious, the present invention interrupts and breaks apart the cycle at both the local anatomical site (the locus of injury) and by preventing the conduction of impulses by sympathetic neurons which innervate the local anatomical area from which the chronic pain originates.

In this manner, the manipulative steps of the present methodology initiate at least one, and preferably a series of, a sympathetic nerve block in the living subject such that the part of the sympathetic nervous system innervating the chronically painful anatomical area becomes blocked and unable to conduct the nerve impulse for a predeterminable time. By the sympathetic nerve blockage, the vasoconstricted blood vessels at the locus of injury become dilated and the other smooth muscle whose overstimulation is the immediate cause of chronic pain become relaxed in measurable degree. Then, after the administration of at least one antagonist of nerve growth factor to the living subject at the local anatomical area, the administered antagonist not only substantially nullifies the neural stimulation effect of such nerve growth factor as is present, but also serves to prevent the nerve growth factor from stimulating other neurons into a hyperactive state. As a consequence of the present therapeutic methodology, those sympathetic and sensory neurons which have been in an overstimulated, hyperactive state begin to revert to normal—thereby reducing the number of impulses carried to the brain which are perceived as chronic pain. Similarly, such chronic pain as is yet perceived does not conduct a new generation of electrical impulses from the central nervous system via the sympathetic nerve fibers because of the sympathetic nerve blockade. Thus, the continual electrical impulse reinforcement cycle is broken and the stimulatory effect of nerve growth factor is neutralized and avoided concurrently. This is believed to be the phenomena which accounts for the major alleviations of chronic pain even in patients suffering from intractable, third stage chronic pain.

III. Benefits And Advantages Of The Present Therapeutic Methodology

By the unique manipulative steps comprising the present invention and the totally unique and previously unknown and original theoretical basis upon which the present methodology relies, a variety of previously unforeseen advantages and major benefits become available. These include:

1. Frequent complete remission of many chronic pain syndromes before they become intractable. These pain syndromes are:
   a. reflex sympathetic dystrophies;
   b. post operative pain syndromes (note perhaps only a third of hand trauma and/or surgeries are completely successful at alleviating chronic pain);
   c. repetitive motion injuries;
   d. non-cardiogenic angina (one third of all angina);
   e. tension and migraine headaches;
   f. facial pain (e.g., temporomandibular joint pain);
   g. low back pain the present treatment of which costs $16 billion dollars a year); and
   h. sports injuries.
2. Early treatment alone could save the following:
   a. loss of work;
   b. personal suffering;
   c. personal financial devastation;
   d. enormous community costs (e.g., insurance); and
   e. broken homes.
3. Reduction in costly and time consuming diagnostic and therapeutic regimes such as:
   a. CAT scans, EMGs, nerve conduction studies, and x-rays;
   b. TENS units, prolonged hospital stay, psychotherapy; and
   c. medications which all have undesirable side-effects.
4. Until this educative process is achieved, millions of past, present, and future victims will reach the so-called intractable stage of chronic pain. The "invention" will possibly help many of them in a logistically manageable format, with immense savings in personal and community suffering and loss.

5. As all diseases may be accompanied by pain and disability, the present invention has a great potential for ameliorating the problems of:
   a. post-traumatic disorders (e.g., head injury);
   b. auto-immune diseases (e.g., arthritis);
   c. post-infection syndromes (e.g., ulcers);
   d. metabolic diseases (e.g., diabetic neuropathy); and
   e. neoplastic disease.
6. The present invention also has enormous potential for relief in all conditions where local or general vasoconstriction occurs (which vasoconstriction inevitably involves a hyperactive sympathetic system), or where sympathetic hyperactivity exists (as determined by diagnostic sympathetic blockade).
7. Where local vasoconstriction decreases the ability to deliver medication to the site of disease, the present invention (by prolonged vasodilation) enables the parenteral use of smaller doses of toxic substances to achieve greater tissue levels with less complication. This potential benefit is great in the chemotherapy of cancer because of its ability to target the tumor (localized or widespread) which in certain instances may be less vascular (i.e., vasoconstricted) than normal tissue.

THE MANIPULATIVE STEPS COMPRISING THE PRESENT THERAPEUTIC METHODOLOGY

Although the present therapeutic methodology has only three requisite manipulative steps, the medical practitioner and clinician will recognize that a great deal of insight and knowledge is required in order to perform each step successfully and in a confident manner. For these reasons, a detailed discussion and review of each manipulative step is presented

A. Identifying The Anatomical Area Of The Patient From Which The Chronic Pain Originates As Being Mediated By The Sympathetic Nervous System The clinician will recognize that the initial step requires him to identify the existence of chronic pain at a specific, localized, anatomical site; and a determination of the chronic pain as being mediated by the sympathetic nervous system. An organized approach thus will include the following:

Complete Patient History
1. Description of problem (in relation to symptoms above and its progression.
2. Onset (work related, spontaneous, disease related).
3. List of physicians and non-physicians (chiropractors, acupunturists, therapists) and their diagnostic procedures, treatments, and effects.
4. Past medical history, including previous traumas and surgeries.
5. Past and present medication history.
6. Allergic history.
7. Present general condition (sleep, activity, work, appetite, bowels, micturition, menstrual history, etc
8. Social history work, expenses, family, stability, transport, change in lifestyle or quality).

A Physical Examination Of The Patient
A physical examination of all relevant systems is performed. It should be unnecessary to inflict pain on the patient during this exam. Observations are made as to swelling, dysfunction, discoloration, and temperature and sweating changes.

An Assessment And Diagnosis Of Chronic Pain
Pain is subjective, therefore, difficult to measure. Reaction may give a clue, though some patients wince at little discomfort while others are impassive in the face of severe pain. Essentially one must believe the patient. Cases of malingering, secondary gain, addiction, and hysteria are probably not common and hopefully become apparent with time.

Appropriate investigations are performed if they could be helpful and if they have not already been done (x-ray, CT scan, bone scan, MRI, EMG, nerve conduction studies, blood work, etc.). It is moot that thermography is definitive.

Note, however, that the only diagnostic procedure that can objectively define sympathetically maintained pain is the effect of one or a series of sympathetic blocks (diagnostic). Accordingly, if the pain is made better or worsened by the sympathetic block, then a component of sympathetic pain exists.

B. Initiating A Sympathetic Nerve Block In The Living Subject Such That The Part Of The Sympathetic Nervous System Innervating The Chronically Painful Anatomical Area Becomes Blocked And Unable To Conduct A Nerve Impulse For A Predeterminable Time Sympathetic nerve blockade is a longstanding and well established technique which can be performed at the spinal cord or the prevertebral sympathetic nerve ganglia. The purpose of the blockade is to interrupt the conduction of electrical nerve impulses along sympathetic nerve fibers at an identifiable, anatomical site and achieve both vasodilation of the local blood vessels and a relaxation in general of the smooth muscles at the locus of injury. An additional advantage conferred by the use of multiple sympathetic nerve blocks is the ability to introduce medications parentally with the expectation that the administered medications will reach those tissues and organs which were previously highly vasoconstricted.

The necessity for sympathetic blockade at ganglia apparently remote from those subtendering the locus of injury arises from the following observations:

1. No hypothesis exists to explain why early reflex sympathetic dystrophies are responsive to appropriate sympathetic blockade, yet late dystrophies become unresponsive, and the pain becomes intractable.
2. It has been observed that dystrophies in the late stages can spread contralaterally (mirror-image pain) and ipsilaterally.
3. As a dystrophy progresses, general signs remote from the locus of injury tend to occur (e.g., falling hair, brittle nails, dry skin, indigestion, cold extremities).

These observations can reasonably be explained by the spread of the hyperactive dystrophic process to neighboring ganglia in the sympathetic chain and eventually could involve the whole sympathetic system. In addition, direct and personal experience over a period of twelve years has demonstrated that many "intractable" late stage dystrophies only respond after *all* sympathetic ganglia are blocked. Indeed, pain in the right hand may only disappear after a final left lumbar sympathetic block follows epidural block, right and then left stellate ganglion blocks, celiac plexus block, and right lumbar sympathetic block. Unfortunately, these patients require this total sympathetic blockade frequently to remain pain free, making the problem relatively unmanageable. It is for these reasons, that following even total sympathetic blockade, it is necessary to employ a nerve growth factor antagonist concurrently—which alone can reach the locus of injury as well as the distant sites involved in pain spread after vasodilation is effected.

The present methodology intends that the conventional methods and practices for inducing one or more sympathetic nerve blocks be utilized without any deviation from customary precautions, anesthetic agents, or general good medical practices. The technique is well documented in the literature as represented by the following publications: *Practical Management Of Pain* (R. Prithri Rij, editor), 1986; *A Synopsis Of Anesthesia*, 10th edition, 1987; *Textbook Of Pain*, second edition, 1989.

Agents Used In Sympathetic Nerve Blockade

In general, local anesthetic agents which reversibly block nerve conduction when applied to nerve tissue are employed. Two general groups of anesthetic agents exist: ester-linked anesthetic agents in which an aromatic residue is separated from an amino group within the chemical structure; and amide-linked agents which contain an amide bond. A representative listing of local anesthetic agents used in sympathetic nerve blocks are provided by Table 1 below.

TABLE 1

AESTHETIC AGENTS

| Surface (Local) Anesthetic | Chemical Name |
|---|---|
| Lidocaine hydrochloride (Xylocaine) | 2-(diethylamiono)-N-(2,6-dimethyl-phenyl)acetamide hydrochloride |
| Cinchocaine; dibucaine hydrochloride (Nupercaine) | 2-butoxy-N-[2-(diethylamino) ethyl]-4-quinoline carboxamide monohydrochloride |
| Benzocaine (ethyl amino-benzoate) | p-aminobenzoic acid ethyl ester hydrochloride |
| Bupivacaine hydrochloride (Marcaine) | dl-1-butyl-2',6'-pipecoloxylidide hydrochloride |
| Mepivacaine hydrochloride (Carbocaine) | N-(2,6-dimethylphenyl)-1-methyl-2-piperidine carboxamide hydrochloride |
| Cocaine hydrochloride | 3-(benzoyloxy)-8-methyl-8-azabi-cyclo-[3,2,1]octane-2-carboxylic acid methyl ester hydrochloride |
| Benoxinate hydrochloride (Oxybuprocaine) | 4-amino-3-butoxybenzoic acid-2-(diethylamino) ethyl ester hydrochloride |
| Prilocaine hydrochloride (Citanest) | N-(2-methylphenyl)-2-(propyl-amino)-propanamide hydrochloride |
| Procaine hydrochloride (Novocain) | 4-aminobenzoic acid-2-(diethyl-amino)ethyl ester hydrochloride |
| Etidocaine hydrochloride (Duranest) | N-(2,6-dimethylphenyl)-2(ethyl-propylamino) butanamide hydrochloride |
| Tetracaine hydrochloride (Pontocaine; Amethocaine) | 4-(butylamino) benzoic acid-2-(dimethylamino) ethyl ester hydrochloride |
| Proparacaine hydrochloride (Alcaine) | 3-amino-4-propoxybenzoic acid-(2-methyl-1-piperidinyl) propyl ester hydrochloride |
| Cyclomethycaine sulfate (Surfacaine) | 4-(cyclohexyloxy)benzoic acid-3-(2-methyl-1-piperidinyl) propyl ester hydrochloride |
| Dyclonine hydrochloride (Dyclone) | 1-(4-butoxyphenyl)-3-(1-piper-dinyl)-1-propanone hydrochloride |

All of the local anesthetic agents listed Within Table 1 are conventionally known, the precautions and contradictions of each also being well described in the scientific literature. For more detailed descriptions and informations for any one of these anesthetic agents, the reader is directed to: Goodman and Gilman, *The Pharmacological Basis Of Therapeutics*, 7th edition, MacMillan Publishing Company, 1985; and Physicians' Desk Reference, 42nd edition, Medical Economics Company, Inc., 1988.

In general, because sympathetic nerve fibers are generally small (2 u or less in diameter) and because the post-ganglionic neuron is unmyelinated while the preganglionic is thinly myelinated, the clinician will find that he needs a smaller use concentration or dosage to effect a sympathetic nerve blockade; and that the nerve block using the smaller dose concentration persists for longer time intervals than are generally achieved when such anesthetic agents are used to block motor or sensory nerve fibers. For purposes of the present therapeutic methodology, the longer the duration of the sympathetic nerve blockade, the better the overall and cumulative result. Accordingly, it is preferred that those local anesthetic agents which provide the greatest time interval and duration for blocking the conduction of nerve impulses be employed.

In addition, it is recognized that the sufficiency, degree, and duration of sympathetic nerve blockade achieved by using local anesthetic agents are also affected by temperature, pH value, electrolyte (sodium, potassium, and calcium) ion levels, and (in some patients) what appears to be an undue sensitivity reaction to local anesthetics. It is thus impossible to predict the actual duration of sympathetic nerve blockade in any given individual with any particular choice of local anesthetic agent until empirically tried. Again, for purposes of the therapeutic methodology, the longer the duration and sufficiency of the sympathetic nerve blockade, the better the overall effect of the methodology.

Initiation Of Sympathetic Nerve Blocks

Sympathetic blockade with local anesthetic agents may be achieved by:

1. Conduction anesthesia (spinal, epidural) extending from T1-2 to L2-3 segmental levels and blocking impulse transmission in primarily the preganglionic sympathetic fibers; and/or 2. Sympathetic ganglionic blockade of some or all of the post-ganglionic fibers emanating from the circa forty-four paired ganglia lying in a chain within the prevertebral fascia along the anterolateral border of the bodies of the vertebrae, as well as the central ganglia (celiac, mesenteric, and hypogastric plexuses). As the chain lies in a potential space a suitable volume of local anesthetic agent injected at several sites into this space has the potential of blocking all the sympathetic ganglia.

As these two approaches to sympathetic blockade are anatomically different, i.e., conduction anesthesia fails to block those post-ganglionic fibers travelling directly to blood vessels as opposed to those travelling with somatic nerves, it is necessary to block both to achieve as total a chemical sympathectomy as desired for the particular problem. The epidural block has the added advantage of providing some anesthesia prior to the decidedly uncomfortable lumbar paravertebral blocks.

Moreover, whereas the post-ganglionic fibers to the head that travel with the carotid, vertebral, and jugular vessels may be blocked at the three cervical sympathetic ganglia, the sympathetic centers in the brain can probably only be blocked with intravenous local anesthetic agents. Their significance in central pain is little understood.

The Technique

It is presumed that sympathetic blocks are only performed by those thoroughly trained in their application, indications, and contraindications, their pertinent anatomy and physiology, the pharmacology of the agents involved, their potential complications, and their course. None should attempt them unless they are confident that they can successfully and expeditiously manage any complication, with ability to maintain an airway, intubate the trachea, if necessary, ventilate the patient, support circulation with position change or crystalloid, colloid, or sympatheticomimetic agents via adequate intravenous access, and prevent aspiration of vomitus.

The patient must be adequately monitored (blood pressure, pulse, respiration, oxygen saturation where appropriate, electrocardiogram) and resuscitative equipment and medication must be on hand (oxygen, Ambu bag, airways, working laryngoscope, endotracheal tubes, masks, pillows, benzodiazapenes Valium, Versed) perhaps thiobarbiturate (Pentothal, Brevital), muscle relaxant (succinyl chlorine), vasopressor (mephentermine, ephedrine, etc. , and narcotic (fentanyl).

The physician performing the block and the supporting nursing staff must understand the importance of calm and gentle encouragement of the patient when a complication occurs, and especially the need for quiet and shielding from bright lights in the face of local anesthetic overdosage. With these provisions: that the physician is adequately trained, competent, and has appropriate facilities, the procedures will be described under optimal and representative conditions.

Procedures

The ideal to be sought is a facility where sympathetic blockade can be maintained continuously over an extended period, or prolonged daily as far as possible. Once the blockade is lifted, the tissue(s) adversely affected by prolonged vasoconstriction will tend to revert to the status quo until an adequate blood flow to those tissues can be maintained to sustain a normal relationship between:

capillary> <extracellular fluid> <cell

This ideal situation would entail an adequately staffed unit to monitor patients:
1. Whose epidural catheters would be infused continuously with local anesthetic solutions by means of a pump;
2. In whom catheters could be placed within the prevertebral fascial space surrounding particular sympathetic ganglia which could be reinjected as the block wore off; and/or
3. Reinjection with longer acting local anesthetic agents which are not yet available.

The intention is to ensure optimal tissue blood flow to provide complete pain relief or evidence of reversal of symptoms prior to parenteral injection of an antagonist for nerve growth factor. Preliminary diagnostic nerve blocks are performed at first in the standard manner as early or minor sympathetically maintained pain may be manageable simply, without resource to this new modality.

Any local anesthetic agent may be used (procaine, lidocaine, bupivacaine, etc.) in equivalent concentrations to ensure sympathetic blockade yet avoid somatic sensory or motor blockade (e.g., lidocaine 0.25%–0.5%, bupivacaine 0.125%–0.25%), the longer acting bupivacaine being preferable except in those rare individuals who are unduly sensitive or those with neurological compromise such as a demyelinating disease. Bupivacaine will last 2–4 hours in the epidural space and 6–12 hours in a ganglionic block, with great individual variation, and therefore blocks should be performed in the morning if the patient is to return to the floor or home in the evening. All patients going home must have an escort and transport.

Epidural Sympathetic Block

In order to block the preganglionic sympathetic fibers from T1-2 to L2-3, the epidural catheter tip is placed ideally at T8-9 through an epidural needle at T9-10 catheter, a bolus of local anesthetic of about 18 ml in young adults or 12 ml in the middle aged will generally achieve a T2-L2 block. A greater volume may be necessary if the level is inadequate. Alternatively, two catheters may be placed at T5-6 and T10-11, with correspondingly lower volumes injected. This will tend to obviate "spotty" epidural blocks. A catheter placed in the lumbar epidural region will required large volumes of local anesthetic. The choice of level of placement depends on the expertise of the physician.

The patient is placed in the lateral decubitus (or sitting) position with the spine flexed to minimize the lumbar lordosis, after intravenous access is assured and the patient's EKG and blood pressure have been monitored. (The patient has signed an informed consent and has emptied the bladder.)

After determining the level to be blocked, the skin is prepared with a bacteriocidal/bacteriostatic agent (e.g., betadine) and the area is draped with sterile towels by the physician wearing sterile gloves. The physician checks his needles, syringes, and local anesthetics and injects appropriately superficial and deep local anesthetic agent (e.g., lidocaine 0.25%–0.5%, 3–5 ml) to the interspinous or paravertebral tissues to provide adequate analgesia prior to epidural needle placement.

The epidural needle is placed in the yellow ligament by either the lateral or mid-line approach, and advanced into the epidural space using loss of resistance to saline or air, or the hanging drop method. The epidural catheter is advanced several centimeters (e.g., 3–5) into the epidural space through the epidural needle, which is then withdrawn. The catheter is checked for the presence of blood or cerebro-spinal fluid, and for free flow (injection of saline), and the catheter is taped securely to the patient's back. The patient is placed in the supine position, and 3–5 minutes after a test dose of about 40 mg (e.g., 3 ml×1.5%) lidocaine containing 1/200,000 epinephrine to ensure that the epidural catheter is not misplaced in a blood vessel or the sub-arachnoid space, the definitive dose of local anesthetic agent to be used (e.g., 15 ml bupivacaine, 0.25%) is injected into the catheter.

Over the next fifteen minutes the patient is watched for:
1. Change in vital signs (blood pressure, pulse rate, and respiratory rate).
2. Change in temperature (hands, feet, face).
3. Development of Horner's syndrome.
4. Subjective change in pain.
5. Change in sensory and motor function.
6. Level of block.

When the patient is stable, he/she may sit up.

The epidural catheter is reinjected every 2–3 hours with a volume of local anesthetic solution (e.g., bupivacaine 0.25%) adjusted upwards or down depending on the level of block.

Prior to ganglionic block in the lumbar region, the epidural catheter may be reinjected with a stronger solution of local anesthetic (e.g., bupivacaine 0.5%, lidocaine 1.0%) to provide more complete sensory block. Otherwise, intravenous sedative and analgesic medication may be necessary.

If the catheter is to be continuously infused by pump, the connection is made under sterile conditions as are any future anipulations involving a break in the line. If the catheter is not to be used until the next day, it and its connections are firmly taped to the patient's body. Reinjections are made under sterile conditions. Any suggestion of contamination demands removal of the catheter.

The site of epidural injection is examined at least every three days for signs of inflammation (redness, swelling, pus) and more often when a higher incidence of infection might be expected (obesity, diabetes, autoimmune deficiency states).

Stellate Ganglion Block

The stellate ganglion may be blocked from the posterior, lateral, or anterior approach, the latter being most commonly chosen. Sympathetic blockade may be obtained at the C6, C7, or T1 transverse process, C7 being the classical approach. The patient may be supine, head up, or in the sitting position. The raised head perhaps allows greater diffusion down the sympathetic chain.

Chassaignac's tubercle (the transverse process of C6) is located opposite the cricoid cartilage, the carotid sheath is retracted laterally and a #22 gauge short beveled needle is placed subcutaneously one centimeter caudad to Chassaignac's tubercle. A local anesthetic skin weal may be made prior to needle placement, but this is not necessary if the needle is placed during expiration. The patient is encouraged to keep as still as possible. The needle is advanced in a consistently perpendicular position until the transverse process is reached or the patient feels pressure in the supraspinatus region of the shoulder, indicating its presence within the stellate ganglion. If the transverse process has been reached, the needle is withdrawn 2 mm (out of longus colli muscle) after which it will lie within the prevertebral fascial plane.

After aspiration tests (for blood, chyle, cerebrospinal fluid, or air), the local anesthetic solution (bupivacaine 0.25%-0..125% or equivalent) is injected expeditiously yet with frequent aspiration. The patient is encouraged to withstand the temporary explosive feeling of pressure in the shoulder which promises effective blockade. 10 ml of local anesthetic solution injected successfully should consistently block the ganglia from C1-T4 If it is desired to block the ganglia to T12, 20 ml of solution may be necessary in the sitting position.

When the patient is stable and the effect (diagnostic or therapeutic) of the block has been evaluated, the opposite stellate ganglion may be blocked in a like manner. Evaluation must consider:
1. Subjective/objective change in symptoms.
2. Presence of Horner's syndrome.
3. Intensification of Horner's syndrome after prior epidural sympathetic block.
4. Increase in temperature of hands and face.
5. Dryness of hands and face.
6. Assessment of immediate potential complication:
   a. Laryngeal block (the patient must not take oral solids or liquids until voice returns).
   b. Hypertension.
   c. Hypertension (beta-blockers may of value though the pressure usually returns to normal quickly and spontaneously, especially if the patient is encouraged to relax).
   d. Pneumothorax (should be obvious by patient coughing on insertion of needle and should rarely require a chest tube).

Celiac Plexus Block

The celiac plexus lies in the mid-line dorsal to the body of the first lumbar vertebra. Autonomic fibers pass through it to most of the viscera. The mesenteric nerves to the mesenteric plexus pass laterally over the body of the twelfth thoracic vertebra. A large volume of local anesthetic agent (bupivacaine 0.125%-0.25%) 40-50 ml should flood the prevertebral fascia extensively in this area.

The patient is placed in the supine position with the lumbar spine flexed, if possible. A large pillow may be placed between the ribcage and the pelvis (the lateral position may also be chosen). The position of the T12-L1 interspinous space is marked A line is drawn from this point below the costal margin to the angle of the ribs and a point 3-3.5 inches from the mid-line marked. Under sterile conditions, a 5-7 inch #20-#22 gauge needle is placed at an angle of 30 degrees along the marked line of the costal margin (after local anesthetic, e.g., lidocaine 0.25% 5 ml is infiltrated if inadequate sensory blockade follows the epidural block). The needle is "walked off" the body of L1 vertebra until it just slips past it, at about an angle of 45 degrees to 60 degrees. The needle is advanced three quarters of an inch. Its stylette is withdrawn, a 20 ml syringe containing bupivacaine 0.25% (or equivalent) attached and after aspiration tests are found to be negative for blood, the solution is injected with frequent aspiration and constant conversation with the patient. After the patient is found to be stable, the block is repeated on the opposite side. The block can be performed from one side using 50 ml solution, but the bilateral approach appears more effective.

Lumbar Sympathetic Block

The classical approach to lumbar sympathetic blockade is to place three needles at L2,3 and 4 ganglia and inject 10 ml local anesthetic solution at each. If blocks are to be performed daily, this would entail considerably more bruising and consequent discomfort. If one 3.5 inch-5 inch #22 gauge needle is placed at L2 or L3 and 20 ml solution injected, a complete lumbar sympathetic block should ensue.

Under sterile conditions, with the patient again placed in the flexed prone (or lateral decubitus) position, L2-3 interspace is identified by counting up from L5-S1 and marked. line perpendicular to the mid-line is drawn and marked at 2-2.5 inches or along the border of the sacro-spinalis group of muscles. If sensory anesthesia from the epidural is inadequate, a skin weal is placed at the marked point and local anesthetic agent infiltrated in the muscle ventrad and mediad. The 3.5-5 inch #22 gauge needle is placed at an angle of 45 degrees to the skin and advanced medially (below the marked line to the L2-3 interspinous space) until it strikes the body of the vertebra. It is then "walked off" the body, increasing the angle of the needle to 60-80 degrees until it is felt to slip past the body. It is then advanced 0.5 of an inch where it should lie in the prevertebral fascial space. 20 ml bupivacaine 0.125%-0.25% (or equivalent) is injected with multiple aspirations to ensure the absence of blood. The patient is kept in conversation throughout injection, and monitored carefully for the next hour After the blocks are completed, the patient is returned to the supine position.

These blocks may be performed under bipolar vision for greater accuracy, which does not seem necessary with proper training when local anesthetics are used. Bipolar vision is mandatory when lytic agents (phenol, alcohol) are injected.

The blocks are sometimes performed under general anesthesia or light sedation which completely obscure the early diagnostic value of sympathetic blockade. Even the selective sympathetic blockade provided by the epidural obscures these effects. The patient is made to understand that the blocks will cause bruising and temporary discomfort.

Prior to injection of local anesthetic agent, the physician must read the label, verify the dilution, and ensure sterility of procedure. In like manner, be sure of any other medication he may inject during the procedure.

Effects Of The Sympathetic Nerve Block

In early sympathetically mediated pain, a sympathetic block may begin to relieve some symptoms without any adverse effects. Where pain or dystrophic change has been present for a long period of time, or soon following drastic injury, some bizarre temporary effects may be seen. These may last from 3–36 hours following a block, but always eventually disappear.

Note, however, that if sympathetic blocks change a pain syndrome, they are diagnostic in that the syndrome is, or contains, a component of sympathetic mediation.

When sympathetic blocks are performed on patients with longstanding, widespread, or devastating pain problems, the following immediate effects may be seen:
1. Some increase or decrease in pain.
2. Increase or decrease in dysesthesiae.
3. Increase or decrease in swelling.
4. Decrease in tone to mimic paralysis.
5. Variable temperature change.

If the decrease in tone affects the intercostal muscles, the patient may be unable to take deep breaths temporarily, although quiet breathing (diaphragmatic) is rarely affected. This may produce panic. Bilateral stellate block may also cause temporary marked swelling of the nasal mucosae and inability to breathe through the nose, which is also frightening to some patients Severe headaches may occur in patients with a history of headaches, possibly as a result of temporary edema. Temporary dizziness or loss of balance may occur. A massive diuresis, inevitable especially with celiac plexus blocks, may produce urinary retention and/or incontinence and require catheterisation. Increased peristalsis may produce abdominal pain and diarrhea. The patient must be kept calm and reassured that these effects are temporary.

Possible Complications Of Sympathetic Blockade

1. Allergy rare with amide-linked local anesthetics).
2. Drug overdosage.
3. Inadvertent intravascular injection (all blocks).
4. Inadvertent somatic block (N.B. laryngeal nerves with stellates).
5. Inadvertent spinal or epidural block.
6. Inadvertent peritoneal injection.
7. Inadvertent puncture of liver, kidney, spleen.
8. Pneumothorax (stellate and celiac plexus block).
9. Bruising and hematoma formation.
10. Hypertension.
11. Hypertension (inadvertent carotid sinus block).
12. Cardiac arrythmias.
13. Epileptiform convulsions (associated with overdosage or intravascular injection.
14. Infection - of greatest significance with epidural abscess.

All these complications are rare in good hands.

All should be manageable without lasting defect in well-trained hands.

Other General Considerations

Whereas decades of experience attest to the known beneficial or curative effects on early sympathetic pain of appropriate blockade, the concomittant enigma exists that this pain with time becomes intractable. The present methodology presumes the necessity to perform blockade at sites remote from the obvious, assuming increasing spread to neighboring ganglia with time, just as it has long been known that symptomatic spread ipsi- and contralaterally occurs (mirror image pain). Thus, when chronic pain which is obviously sympathetic proves refractory to apparently appropriate sympathetic blockade, it is logical to extend that blockade to neighboring ganglia.

When performing extensive or even "total" sympathetic blockade, a logical sequence usually is apparent. For example, if the sympathetic pain originated in the right arm, the obvious sequence of blockade would be right stellate > left stellate > right celiac > left celiac > right lumbar sympathetic > left lumbar sympathetic ganglia. Suitable volumes are used to try to ensure blockade of all ganglia. With each successive block, immediate changes are noted with relation to the original, as well as distant, sites of pain. With each day of blocks, changes and their duration and extent are noted; and with each week following block prolongation of beneficial effect to the original pain state are noted, giving an idea of what plan is necessary to proceed.

C. Administering An Antagonist Of Nerve Growth Factor To The Living Subject Whereby The Administered Antagonist Substantially Nullifies The Neuron Stimulation Effect Caused By Such Nerve Growth Factor As Is Present The final manipulative step of the present therapeutic methodology requires the administration of an effective amount of an antagonist of nerve growth factor to the patient. The intended effect of the administered antagonist is to substantially nullify the neural stimulation effect initiated by nerve growth factor; or to neutralize the hyperactive synaptic state which is the consequence of nerve growth factor action on the neuron. The term "antagonist" thus represents any biologically active chemical composition which when introduced to the living subject actively opposes and contradicts either the presence or the consequences of nerve growth factor on a sympathetic or sensory nerve fiber. The term "antagonist" thus implies no specific mechanism of biological action whatsoever; and is deemed to expressly include and encompass all possible pharmacological, physiological, and biochemical interactions against nerve growth factor and its consequences which can be achieved by a variety of different, and chemically divergent, compositions.

Accordingly, there are many different kinds of nerve growth factor antagonists possible which are suitable for use with the present therapeutic methodology. One category is represented by the vinca alkaloids which function as blocking agents and prevent the retrograde axonal uptake of nerve growth factor along the nerve fiber in-vivo. A second, different category is represented by colchicine, which is a superoxidation inhibitor which prevents the growth, diffuse elaboration, and synaptic contact with target cells and/or organs despite the neuron being in an overly-stimulated, hyperactive state. A third category is represented by the known polyclonal or monoclonal anti-nerve growth factor antibodies conventionally known and described in the literature which are recognized as being able to neutralize nerve growth factor molecules directly upon reactive contact. A fourth category is represented by the compounds guanethidine, reserpine, and 6-hydroxydopamine - all of which function as synaptic inactivators of norepinephrine (or noradrenaline) and spinephrine, the neurotransmittors dominating sympathetic nerve cells.

In addition to these, it is expected that a number of other categories of antagonistic agents able to nullify or neutralize nerve growth factor will be identified if sought for by the clinician. These other categories include: dissociative agents such as protease enzymes which are specific for the nerve growth factor polypeptide structure; preventative agents such as specific compounds or specific antibodies selected for the receptor proteins on the nerve fiber which act as receptor sites for the nerve growth factor itself prior to its retrograde migration up the axon of the neuron; curative agents which are chemical compositions which are able to complex with or otherwise chemically react with nerve growth factor to form reaction products and reaction complexes which are pharmacologically and physiologically inactive; and biochemical retardants which would function by interacting with the cells and tissues at the anatomical area where the original locus of injury occurred in order to diminish or cause or avoidance of the initial synthesis and release of nerve growth factor by those target cells. For purposes of the present invention, it will be explicitly understood that the term "antagonist" encompasses all the previously identified terms, titles, and functional states and characteristics whereby the nerve growth factor itself, its ability to stimulate nerve cells and induce the hyperactive neural condition, or the consequences of the hyperactive neuron are substantially nullified or neutralized in any meaningful degree.

Modes of Administering the Antagonist To The Living Subject

Any mode of administration conventionally known which causes the antagonist to be present in an effective concentration or amount in the chronically painful anatomical area is a suitable mode of administration for purposes of practicing the present invention. One preferred mode of administration is via the parenteral route whether by syringe injection or direct intravenous flow introduction. It is intended that the antagonist would be prepared in sterile format; in multiple or single dose units; and typically appear dispersed in a fluid carrier such as sterile physiological saline or 5% dextrose solutions commonly used with injectables.

Another favored route of administration is via iontophoresis. The modern technique and commercially available kinds and varieties of apparatus for delivering therapeutic agents by iontophoresis is well known [see for example, U.S. Pat. No. 4,702,732 and the individual references cited therein]. In addition, the iontophoretic delivery of vinca alkaloids is documented in the scientific literature [Csillik et al., *Neuroscience Letters* 31:87-90 (1982); Rossano et al., *The Pain Clinic* 3:31-36 (1989)].

While these remain the preferred modes of administration at the present time, the present invention intends that any mode of administration which presents a nerve growth factor antagonist in an effective concentration at the chronically painful anatomical site to be suitable for use. All such alternative modes of administration are deemed to be within the scope of the present invention.

In addition, the optimal or efficacious dosages and concentrations of each kind of antagonist of nerve growth factor will, per force, be determined experimentally. While pharmacologically active concentrations and dosages of vinca alkaloids, colchicine, polyclonal and monoclonal anti-nerve growth factor antibodies, guanethidine, reserpine, and 6-hydroxydopamine are recognized and decreed both by authoritative text and research investigations reported in the scientific literature, the present therapeutic methodology is expected to require a much lower dosage in each instance and for each category of antagonist than that normally employed for the conventionally known usage or application of that composition. In this manner, particularly where the chosen antagonist has severe or detrimental side or toxic effects (such as the vinca alkaloids) the general risk of exposing the patient and incurring undesired toxic or hazardous side complications is greatly decreased by following the principles of the present therapeutic methodology.

Some Preferred Antagonists Of Nerve Growth Factor

1. The vinca alkaloids: Four vinca alkaloids are known: vinblastine, vincristine, vinleurosine, and vinrosidine. Only two of these, vinblastine and vincristine, have been extensively reviewed by clinical investigations. Comprehensive reviews of the vinca alkaloids have, however, been published: Johnson, I.S., "Plant Alkaloids," in *Cancer Medicine,* (Holland, J. F. and Frei, E., III, editors), Lea and Febiger, Philadelphia, 1973, pp 840-850; Johnson, I. S., Armstrong, J. G., Gorman, M., and Burnett, J. P., "The Vinca Alkaloids: A New Class of Oncolytic Agents," *Cancer Res.* 23:1390-1427 (1963); Symposium (various authors), "Vincristine," *Cancer Chemother. Rep.* 4(3):1-82 (1973); and Creasey, W. A., "Vinca Alkaloids and Colenicine," in *Anterioplastic and Immunosuppressive Agents,* Part II (Sartorelli, A. C. and Johns, D. G., editors), Springer-Verlag, Berlin, 1975b, pp 670-694.

The four vinca alkaloids are very similar chemically. The are asymmetrical, dimetric compounds of the structure:

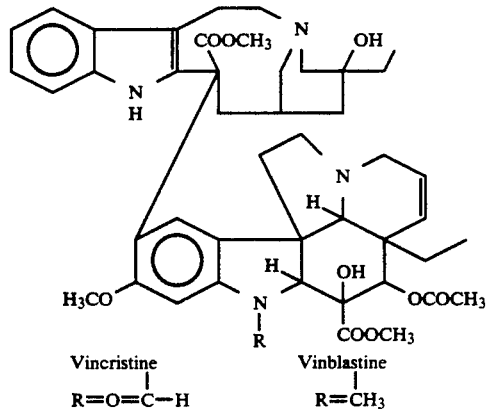

The presently known therapeutic uses and FDA approved applications for the vinca alkaloids are as therapeutic agents in the treatment of lymphosarcoma, reticulum-cell sarcoma, mycosis fungoides, acute and chronic leukemias, neuroblastoma, as well as in carcinomas of the breast, lung, oral cavity, testis, and bladder. The vinca alkaloids are also employed in treating Hodgkin's disease, Kaposi's sarcoma, Letter-Siwe disease, choriocarcinoma, and Wilson's tumor [The *Pharmacological Basis of Therapeutics*, 8th edition,, MacMillan Publishing Co., 1990]. As noted previously, some research investigators have experimented with vinca alkaloids for the treatment of pain.

2. Colchicine: Colchicine is recognized as an anti-inflammatory agent which is pharmacologically effective only against gouty arthritis. It provides dramatic relief of acute attacks of gout and is an effective prophylactic agent against such attacks. It is not recognized as an analgesic and does not provide relief of other types of pain. Colchicine is also employed as a research tool via its capability as an antimitotic agent. It is widely employed as an experimental tool in the study of normal and abnormal cell division and cell function.

The structural formula of colchicine is as follows:

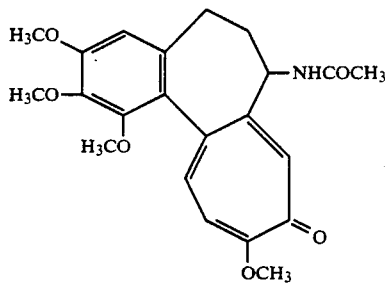

Aside from its use for the relief of acute attacks of gout, colchicine is employed because it can arrest plant and animal cell division both in-vitro and in-vivo. Mitosis is arrested in the metaphase, due to failure of spindle formation. Bizarre and often abnormal nuclear configurations ensue and the cells then often die.

Other effects of colchicine include: the ability to inhibit the relief of histamine-containing granules from mast cells under varying conditions; the ability to lower body temperature; the ability to increase the sensitivity of the body to central depressants; and the ability to depress the respiratory center.

3. Guanethidine, Reserpine, And 6-hydroxydopamine: All of these are noradrenaline or norepinephrine inhibitors or blocking agents which interfere with the chemical synapse at postganglionic adrenergic nerve endings. Each of these, however, acts via different mechanisms, including depletion of the neurotransmittor and direct prevention of its release. However, these compounds appear to act by more than one mechanism in many instances.

Guanethidine is considered one composition representative of drugs that depress the function of postganglionic adrenergic nerves. Guanethidine and related compounds such as bretylium have a strongly basic moiety such as the guanethidine grouping or a quaternary nitrogen. The major effect of guanethidine is inhibition of responses to stimulation of sympathetic nerves and to indirectly acting simple sympathometic amines. The site of this inhibition is clearly presynaptic and caused by impaired release of neurotransmittor from adrenergic neurons.

Reserpine is a rauwolfia alkaloid with a complex structure. Reserpine deletes stores of catecholamines and 5-hydroxytryptophane. Most of its pharmacological effects are attributed to this action and most of the catecholamine is deaminated intraneurally. Major impairment of adrenergic nerve function occurs quickly within one hour's duration and is maximal by twenty-four hours' time. Its current therapeutic uses are in the treatment of hypertension because relatively large doses of reserpine cause a slowly developing fall in blood pressure after parenteral administration.

4 Anti-Nerve Growth Factor Antibodies: The preparation and use of polyclonal anti-nerve growth factor antisera raised in rabbits is well documented in the scientific literature [Windebank, A. and J. Poduslo, *Brain Research* 385:197-200 (1986)]. As noted therein, different anti-nerve growth factor antisera when combined with nerve growth factor completely inhibited neurite outgrowth at very high dilution concentrations. The ability to neutralize the pharmacological effects of nerve growth factor via specific antisera has been a favorite experimental technique [Richardson, P. and T. Ebendal, *Brain Research* 246:57-64 (1982); Riopelle *et al.*, *Neurosci. Lett.* 25:311-316 (1981); Levi-Montalcini, R. and B. Booker, *Proc. Natl. Acad. Sci. U.S.A.* 46:373-384 (1960)]. All conventionally available and known methods for preparing both polyclonal and monoclonal antibodies specific against nerve growth factor are deemed to be suitable for use; all such anti-nerve growth factor preparations are deemed to be within the scope of the present invention.

IV Suggested Protocol For Therapeutic Methodology

A short protocol is provided hereinafter whose procedural steps will provide the medical practitioner or clinician with the information and knowledge to perform the therapeutic methodology successfully. The preferred protocol is as follows:

1. Patient accepted by referral.
2. Review of history, investigations, and therapies.
3. Physical examination, further investigation as appropriate.
4. Assessment of risk, with attempt to stabilize high-risk patients under aegis of primary physician.
5. Receipt of informed consent.
6 Placement of intravenous line and suitable monitors (blood pressure, EKG, temperature O₂ analyzer).
7. Check of resuscitative equipment (oxygen, ventilator bag, endotracheal tube, laryngoscope, muscle relaxant, anti-convulsant, anti-emetic, albumen, vasopressors, antihistamines).
8. Provision of sedation when necessary.
9. Placement of selective segmental epidural catheter to block sympathetics (T2-L2). Injection of low concentration, long-acting low anesthetic (c. 15 ml).
10. When patient is stable, placement of sympathetic ganglion blocks (using appropriate volumes of low-concentration, long-acting local anesthetic) starting at the ganglion appropriate to the locus of injury, and extending the ganglia blocked progressively (contralaterally. and ipsilaterally) to achieve effective symptomatic relief.
11. Continuous monitoring and treatment with appropriate intravenous fluids and albumen.
12. Continual reassurance of patient. of sympathetic spread,
13. Noting of other evidence including duration and severity of pain and other dystrophic signs, unexpected (temporary) hypotonicity of muscle groups following blocks, temperature, and color changes.

14. In some cases of severe, prolonged pain, these blocks may need to be repeated daily for several days until optimal pain relief has been established prior to use of vinca. Ideally, the epidural catheter would be infused continuously.

15. When total sympathetic blockade is achieved (or partial, when appropriate), as soon as possible, vinca will be infused through a large vein in doses less than the normal oncological doses (vinblastine 3.7-11 mg/m$^2$ no more frequently than once every 7 days; vincristine 1.4 mg/m$^2$).

16. Assessment of results of therapy will be made over the next three days then weekly. Need for repeated therapy will be based on patient tolerance and return of symptoms.

17. Patient will also be monitored for side-effects such as hypesthesiae, leukopenia, and constipation. Any rare side-effect will be noted, as well as its persistence.

CASE HISTORIES

To demonstrate the efficacy and unexpected benefits of the present therapeutic methodology, several individual case histories involving human patients are provided hereinafter. It will be expressly understood, however, that these individual case histories are merely representative of the unusual results and unique advantages provided by the present invention.

Case History 1

Patient ZW is a woman aged 47 years and diagnosed as having multiple myeloma of the lower lumbar spine and sacrum. Two months prior to admission to the hospital, she presented evidence of dysesthesia of both legs; and, following diagnosis, was treated with chemotherapy and x-ray therapy to the spine. After leaving the hospital, the woman suffered a fall and was readmitted to the hospital with severe hip pain which stread from the right to the left, and showed progressive coccygeal pain.

On May 16 of that year, the patient was noted to have dyspnea, malaise, anorexia, nausea and vomiting, anemia, hypercalcemia, and renal insufficiency. Her legs were hyporeflexic with decreased sensation to pin-prick below the knees. Myelogram showed concentric narrowing of the dural sac at LS-Sl and extradural compression especially arteriorly. By June 13 of that year, she had not been out of bed for two consecutive weeks and could not move either her hips or knees. The woman was receiving daily 450 mg of morphine, plus dilaudid phenothiazines and tricyclic antidepressants.

On June 13 of that year, a thoracic epidural catheter was placed at T12-Ll and 5 ml of 0.5% xylocaine was injected. The patient felt an immediate relief of pain and could begin to move her legs freely. Upon subsequent injection of 15 ml of 0.25% bupivacaine, the patient was able to sit up and her pain relief increased substantially in comparison to her usual state. The next day, 18 hours later, the patient was able to physically get out of bed and was able to walk for the first time in two calendar weeks. The patient estimated she had approximately 50% pain relief upon sitting down.

Subsequently, the thoracic epidural catheter was reinjected with 15 ml of 0.25% bupivacaine, and bilateral lumbar sympathetic blocks as well as a celiac plexus block were performed using a total of 70 ml of 0.25% bupivacaine. Within one hour's time, while sympathetic nerve block was maximum and could be predicted to last at least six hours, vincristine [2 mg/m$^2$ of body surface area in 100 ml of normal saline] was administered intravenously and continued for approximately four calendar days. Once the sympathetic nerve blocks were completed, the patient expressed that she was pain free; and continued to remain almost completely pain free for three calendar months thereafter. Her dysesthesiae had disappeared by the following day after treatment; and the patient both moved and walked freely without pain. Consequently, she was weaned of morphine over the next week and was sufficiently comfortable to take a vacation by herself without aid from any other person. Nine calendar months later, the patient was reported to be essentially pain free and continuing to be able to move and walk freely.

Case History 2

Patient JM was a 40 year old male with a ten year history of multiple myeloma in all his bones, 5 vertebral fractures, and metal rods in his right humerus and left femur. The patient reported severe pain at all times whether sitting, walking, or lying down. Patient JM was given epidural, lumbar, celiac, and stellate bilaterally sympathetic nerve blocks; and was subsequently parenterally administered vincristine [2 mg/m$^2$ of body surface area in 100 ml of normal saline]. Patient JM experience an immediate reduction of pain and was markedly far more comfortable and relatively pain free one week later.

Case History 3

Patient MD is a 36 year old male who was unable to work following a fall down stairs approximately 15 months ago. He complained of constant pain from his right buttock (at the sacroiliac joint) spreading with time to his right loin, leg, and ankle When examined, his back was swollen; straining at stool and micturition were painful; and cold weather made his pain worse. His feet were getting colder progressively since the time the injury occurred. Physical therapy was given but did not help the patient; hot baths and Feldene were said to help only a little.

For four weeks duration, Patient MD received weekly nerve blocks (thoracic epidural, bilateral lumbar sympathetic, and bilateral celiac plexus) with only temporary and marginal pain relief. Subsequently, a procedure was initiated in which these earlier given blocks were repeated and bilateral stellate ganglion blocks added; after which 1 mg of colchicine was immediately injected intravenously. Patient MD experienced a total loss of pain; and remains presently pain-free after the passage of six weeks time.

Case History 4

Patient WS is a 55 year old male who has suffered constant and shooting pains in the right side of his face since a composite resection of a squamous cell carcinoma of the floor of the mouth was performed nine months ago. His operation then included partial resection of the mandible and tongue, and dissection of the neck. Five months after the composite resection, Patient WS received a six-week course of radiation therapy.

After the operation, patient WS's facial pains have become worse with time; and he can not sleep or chew food. Percocet provides only one hour of partial relief. He has severe limitation of movement of his jaw and his neck; and very recently his pain has spread to his right shoulder.

Nine months after the operation, a procedure was initiated during which 20 ml of 0.25% Bupivacaine was injected on each side for a bilateral stellate ganglion block; which was followed immediately by the intravenous injection of 1.0 mgcolchine dissolved in 10 ml of normal saline. Patient WS experienced significant improvement in the movement of his jaw and neck. He also had 60 hours of major pain relief despite the fact that the dosage of Bupivacaine administered could only be expected to last 6 hours.

The present invention is not to be restricted in form nor limited in scope except by the claims appended hereto.

What we claim is:

1. A therapeutic method for alleviating sympathetically mediated chronic pain in a living subject, said therapeutic method comprising the steps of:
    identifying the anatomical area of the living subject from which the chronic pain originates as being mediated by the sympathetic nervous system;
    initiating at least one sympathetic nerve block to the living subject such that the part of the sympathetic nervous system innervating said chronically painful anatomical area becomes blocked and unable to conduct a nerve impulse for a predeterminable time; and
    administering an effective amount of at least one antagonist of nerve growth factor to said chronically painful anatomical area of the living subject whereby said administered antagonist nullifies the neuron stimulation effect of such nerve growth factor as is present at said chronically painful anatomical area.

2. The therapeutic method as recited in claim 1 wherein said sympathetic nerve block is initiated in the epidural space of the living subject.

3. The therapeutic method as recited in claim 1 wherein said sympathetic nerve block is initiated in the sympathetic ganglia of the living subject.

4. The therapeutic method as recited in claim 1 wherein said sympathetic nerve block is initiated via the administration of at least one local anesthetic agent.

5. The therapeutic method as recited in claim 1 wherein said antagonist of nerve growth factor is a vinca alkaloid.

6. The therapeutic method as recited in claim 1 wherein said antagonist of nerve growth factor is colchicine.

7. The therapeutic method as recited in claim 1 wherein said antagonist of nerve growth factor is selected from the group consisting of guanethidine, reserpine, and 6-hydroxydopamine.

8. The therapeutic method as recited in claim 1 wherein said antagonist of nerve growth factor is at least one antinerve growth factor antibody.

9. The therapeutic method as recited in claim 1 wherein said antagonist of nerve growth factor is administered parenterally.

10. The therapeutic method as recited in claim 9 wherein said parenteral administration is intravenous administration.

11. The therapeutic method as recited in claim 9 wherein said parenteral administration is by iontophoresis.

* * * * *